(12) United States Patent
Frey et al.

(10) Patent No.: US 9,006,479 B2
(45) Date of Patent: Apr. 14, 2015

(54) PROCESS FOR PREPARING POLYOL ESTERS

(75) Inventors: Guido D. Frey, Reidstadt (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 297 days.

(21) Appl. No.: 13/499,176

(22) PCT Filed: Sep. 17, 2010

(86) PCT No.: PCT/EP2010/005728
§ 371 (c)(1),
(2), (4) Date: Mar. 29, 2012

(87) PCT Pub. No.: WO2011/042116
PCT Pub. Date: Apr. 14, 2011

(65) Prior Publication Data
US 2012/0190883 A1     Jul. 26, 2012

(30) Foreign Application Priority Data
Oct. 8, 2009 (DE) .......................... 10 2009 048 775

(51) Int. Cl.
*C07C 67/08* (2006.01)
(52) U.S. Cl.
CPC ..................................... *C07C 67/08* (2013.01)

(58) Field of Classification Search
CPC ...................................................... C07C 67/08
USPC .......................................................... 560/182
See application file for complete search history.

(56) References Cited

U.S. PATENT DOCUMENTS

| | | | | |
|---|---|---|---|---|
| 2,628,249 A | | 2/1953 | Bruno, Jr. ...................... | 260/475 |
| 4,526,725 A | * | 7/1985 | Deardorff ........................ | 556/56 |
| 5,324,853 A | * | 6/1994 | Jones et al. ..................... | 560/98 |

FOREIGN PATENT DOCUMENTS

| | | |
|---|---|---|
| EP | 0 356 255 A2 | 2/1990 |
| EP | 356255 A2 * | 2/1990 |

OTHER PUBLICATIONS

K.L. Williamson, "Synthesis of Isobutyl Propionate via Esterification", Macroscale and Microscale Organic Experiments, 2nd Ed. 1994, Boston p. 385; revised Mar. 19, 2002.*

* cited by examiner

*Primary Examiner* — Yong Chu
(74) *Attorney, Agent, or Firm* — Michael W. Ferrell

(57) ABSTRACT

The present invention relates to a process for preparing polyol esters by reacting polyols with linear or branched aliphatic monocarbocxylic acids having 3 to 20 carbon atoms, the reaction taking place in the presence of a Lewis acid comprising at least one element from groups 4 to 14 of the Periodic Table of the Elements as catalyst, and in the presence of an adsorbent, the reaction product being subjected subsequently to a steam treatment.

34 Claims, No Drawings

PROCESS FOR PREPARING POLYOL ESTERS

CLAIM FOR PRIORITY

This application is based on prior application No. PCT/EP2010/005728, filed Sep. 10, 2010 which was based on German Patent Application No. DE 10 2009 048 775.1, filed Oct. 8, 2009. The priorities of the foregoing applications are hereby claimed and their disclosures incorporated herein by reference.

TECHNICAL FIELD

The invention relates to a process for preparing polyol esters from linear or branched aliphatic monocarboxylic acids having 3 to 20 carbon atoms and polyols by converting the starting compounds in the presence of a Lewis acid containing at least one element of groups 4 to 14 of the Periodic Table of the Elements as a catalyst.

BACKGROUND

Esters of polyhydric alcohols, also known as polyol esters, find a variety of uses on a large scale in industry, for example as plasticizers or lubricants. The selection of suitable starting materials allows the physical properties, for example boiling point or viscosity, to be controlled, and the chemical properties, such as hydrolysis resistance or stability to oxidative degradation, to be taken into account. Polyol esters can also be tailored to the solution of specific performance problems. Detailed overviews of the use of polyol esters can be found, for example, in Ullmann's Encyclopaedia of Industrial Chemistry, 5th edition, 1985, VCH Verlagsgesellschaft, Vol. A1, pages 305-319; 1990, Vol. A15, pages 438-440, or in Kirk Othmer, Encyclopaedia of Chemical Technology, 3rd edition, John Wiley & Sons, 1978, Vol. 1, pages 778-787; 1981, Vol. 14, pages 496-498.

The use of polyol esters as lubricants is of great industrial significance, and they are used particularly for those fields of use in which mineral oil-based lubricants meet the requirements set only incompletely. Polyol esters are used especially as turbine engine and instrument oils. Polyol esters for lubricant applications are based frequently on 1,3-propanediol, 1,3-butanediol, 1,4-butanediol, 1,2-hexanediol, 1,6-hexanediol, neopentyl glycol, trimethylolpropane, pentaerythritol, 2,2,4-trimethylpentane-1,3-diol, glycerol or 3(4)-8(9)-dihydroxymethyltricyclo[5.2.1.0$^{2,6}$]-decane, also known as TCD alcohol DM, as the alcohol component.

Polyol esters are also used to a considerable degree as plasticizers. Plasticizers find a variety of uses in plastics, coating materials, sealing materials and rubber articles. They interact physically with high molecular weight thermoplastic substances, without reacting chemically, preferably by virtue of their swelling and dissolution capacity. This forms a homogeneous system, the thermoplastic range of which is shifted to lower temperatures compared to the original polymers, one result being that the mechanical properties thereof are optimized, for example deformation capacity, elasticity and strength are increased, and hardness is reduced.

In order to open up the widest possible fields of use to plasticizers, they must fulfil a series of criteria. They should ideally be odourless, colourless, and light-, cold- and heat-resistant. Moreover, it is expected that they are insensitive to water, comparatively non-flammable and not very volatile, and are not harmful to health. Furthermore, the production of the plasticizers should be simple and, in order to meet ecological requirements, avoid waste substances, such as by-products which cannot be utilized further and wastewaters comprising pollutants.

A specific class of polyol esters (they are referred to as G esters for short) contains diols or ether diols as the alcohol component, for example ethylene glycol, diethylene glycol, triethylene glycol, tetraethylene glycol, 1,2-propylene glycol or higher propylene glycols. They can be prepared in different ways. In addition to the reaction of alcohol and acid, optionally in the presence of acidic catalysts, further processes are employed in practice to obtain G esters, including the reaction of diol with acid halide, the transesterification of a carboxylic ester with a diol, and the addition of ethylene oxide onto carboxylic acids (ethoxylation). In industrial manufacture, only the direct reaction of diol and carboxylic acid and the ethoxylation of carboxylic acids have become established as production processes, preference usually being given to the esterification of diol and acid. This is because this process can be performed with no particular complexity in conventional chemical apparatus, and it affords chemically homogeneous products. Compared to this, ethoxylation requires extensive and costly technical equipment. Ethylene oxide is a very reactive chemical substance. It can polymerize explosively and forms explosive mixtures with air within very wide mixing ranges. Ethylene oxide irritates the eyes and respiratory pathways, leads to chemical burns and to liver and kidney damage, and is carcinogenic. The handling thereof therefore entails extensive safety measures. Moreover, scrupulous cleanliness of storage apparatus and reaction apparatus has to be ensured, in order to rule out the formation of undesired impurities as a result of side reactions of the ethylene oxide with extraneous substances. Finally, the reaction with ethylene oxide is not very selective, since it leads to mixtures of compounds of different chain length.

The direct esterification of alcohols with carboxylic acids is one of the basic operations in organic chemistry. In order to increase the reaction rate, the conversion is typically performed in the presence of catalysts. The use of one of the reactants in excess and/or the removal of the water formed in the course of the reaction ensures that the equilibrium is shifted in accordance with the law of mass action to the side of the reaction product, i.e. of the ester, which means that high yields are achieved.

Comprehensive information regarding the preparation of esters of polyhydric alcohols, also including esters of ethylene glycols and fatty acids, and regarding the properties of selected representatives of these compound classes can be found in Goldsmith, Polyhydric Alcohol Esters of Fatty Acids, Chem. Rev. 33, 257 ff. (1943). For example, esters of diethylene glycol, of triethylene glycol and of polyethylene glycol are prepared at temperatures of 130 to 230° C. over reaction times of 2.5 to 8 hours. To remove the water of reaction, carbon dioxide is used. Suitable catalysts mentioned for the esterification of polyhydric alcohols are inorganic acids, acidic salts, organic sulphonic acids, acetyl chloride, metals or amphoteric metal oxides. The water of reaction is removed with the aid of an entraining agent, for example toluene or xylene, or by introducing inert gases such as carbon dioxide or nitrogen.

The production and the properties of fatty acid esters of the polyethylene glycols are discussed by Johnson (edit.), Fatty Acids in Industry (1989) Chapter 9, Polyoxyethylene Esters of Fatty Acids, and a series of preparative hints are given. Higher diester concentrations are achieved by the increase in the molar ratio of carboxylic acid to glycol. Suitable measures for removing the water of reaction are azeotropic distillation in the presence of a water-immiscible solvent, heating while passing through an inert gas, or performing the reaction under reduced pressure in the presence of a desiccant. When the addition of catalysts is dispensed with, longer reaction times and higher reaction temperatures are required. Both reaction conditions can be made milder by the use of catalysts. In addition to sulphuric acid, organic acids such as p-toluenesulphonic acid and cation exchangers of the polystyrene type are the preferred catalysts. The use of metal powders, such as tin or iron, is also described. According to the teaching from U.S. Pat. No. 2,628,249, colour problems in the case of catalysis with sulphuric acid or sulphonic acid can be alleviated when working in the presence of activated carbon.

Further metallic catalysts used to prepare polyol esters are also alkoxylates, carboxylates or chelates of titanium, zirconium or tin, for example according to U.S. Pat. No. 5,324,853 A1. Such metal catalysts can be considered as high-temperature catalysts, since they achieve their full activity only at high esterification temperatures, generally above 180° C. They are frequently added not at the start of the esterification reaction, but after the reaction mixture has already been heated up and has reacted partly with elimination of water. In spite of the relatively high reaction temperatures and relatively long reaction times required compared to the conventional sulphuric acid catalysis, crude esters with a comparatively low colour number are obtained in the case of catalysis with such metal compounds. Common esterification catalysts are, for example, tetra(isopropyl) orthotitanate, tetra(butyl) orthotitanate, tetra(butyl) zirconate or tin(II) 2-ethylhexanoate.

The catalytic esterification reaction of polyols with carboxylic acids achieves, based on the component present in deficiency, a high conversion within a comparatively short time, but a comparatively long reaction time has to be accepted for the remaining conversion to the desired polyol esters. Although a polyol ester is obtained with an acceptable residual content of partly esterified products, expressed by the hydroxyl number in mg KOH/g (to DIN 53240) or by the content of partly esterified products determined by gas chromatography, long reaction times are economically disadvantageous since they limit the performance of the industrial production plant. In order also to accelerate the residual conversion, U.S. Pat. No. 5,324,853 A1 proposes intensive mixing of the reaction mixture.

After the esterification reaction has ended, sufficient removal of the metal catalyst has to be ensured, since metal traces in the purified polyol esters can impair the use thereof as plasticizers or lubricants by, for example, influencing the electrical conductivity or the stability to atmospheric oxygen. According to the procedure from U.S. Pat. No. 5,324,853 A1, the crude esterification mixture is admixed with an aqueous sodium carbonate solution and optionally with activated carbon. This procedure hydrolyses the metal compounds to insoluble solids, which can be filtered off before the further workup of the crude ester compound.

According to U.S. Pat. No. 4,304,925 A1, the crude esterification product, before addition of alkali, is first admixed with water and treated under hot conditions. This converts the hydrolysed metal compounds to readily filterable precipitates.

EP 0 356 255 A2 discusses the esterification of propoxylated glycerol and saturated or unsaturated $C_{10}$-$C_{24}$ fatty acids in the presence of tin catalysts and titanate catalysts. The crude ester is treated with sodium hydroxide solution and then filtered in the presence of a filtration aid.

U.S. Pat. No. 4,526,725 A1 discloses chelated alkyl titanate catalysts and the use thereof as an esterification catalyst. The crude ester is subjected to a steam distillation to remove alcohol residues.

The prior art for preparation of polyol esters under metal catalysis requires either a special reactor design in order to complete the esterification reaction within an economically acceptable time, or an additional treatment with water under hot conditions, in order to substantially completely remove the metallic catalyst after the esterification reaction has ended with formation of hydrolysis products which can be filtered off readily.

It was therefore an object of the present invention to improve the known processes and to optimize the process by adjusting and simplifying the successive component steps of the overall process, and to simplify the production of polyol esters in high quality, such that polyol esters can have a maximum variety of applications.

SUMMARY OF INVENTION

The invention therefore consists in a process for preparing polyol esters by reacting polyols with linear or branched aliphatic monocarboxylic acids having 3 to 20 carbon atoms, characterized in that a mixture of the starting compounds is allowed to react in the presence of a Lewis acid containing at least one element of groups 4 to 14 of the Periodic Table of the Elements as a catalyst with removal of the water formed, the starting compounds being converted in the presence of an adsorbent, and then a steam treatment is performed.

DETAILED DESCRIPTION

The invention is described in detail below with reference to several embodiments and numerous examples. Such discussion is for purposes of illustration only. Modifications to examples within the spirit and scope of the present invention, set forth in the appended claims, will be readily apparent to one of skill in the art. Terminology used throughout the specification and claims herein is given its ordinary meaning for example, hPa refers to hectopascals (absolute) unless otherwise indicated.

The reaction between the polyol and aliphatic monocarboxylic acid starting compounds, depending on the starting materials, sets in within the range from about 120 to 180° C., and can subsequently be conducted to completion in different ways.

In one configuration of the process according to the invention, the mixture is first heated proceeding from room temperature to a temperature up to a maximum of 280° C., preferably up to 250° C., and the pressure is lowered stage by stage proceeding from standard pressure with the temperature kept constant, in order to facilitate the removal of the water of reaction. The selection of the pressure stages, whether one, two or more than two stages, and of the pressure to be established at a particular stage, can be varied over a wide range and matched to the particular conditions. For example, in a first stage, the pressure can be lowered proceeding from standard pressure first down to 600 hPa, and then the reaction can be conducted to completion at a pressure of 300 hPa. These pressure figures are guide values which are appropriately complied with.

In addition to the variation of the pressure, it is likewise also possible to alter the temperature in one, two or more than two stages proceeding from room temperature during the esterification reaction, such that the temperature is increased from stage to stage at constant pressure, typically up to a maximum temperature of 280° C. However, it has been found to be appropriate to heat to a maximum of 280° C. with rising temperature from stage to stage, and also to lower the pressure from stage to stage. For example, the esterification reaction can be conducted proceeding from room temperature in a first stage at a temperature up to 190° C. A reduced pressure down to 600 hPa is likewise applied, in order to accelerate the driving-out of the water of reaction. On attainment of the temperature stage of 190° C., the pressure is lowered once again down to 300 hPa, and the esterification reaction is conducted to completion at a temperature up to 250° C. These temperature and pressure figures are guide values which are appropriately complied with. The temperature and pressure conditions to be established at the particular stages, the number of stages and the particular temperature increase or pressure reduction rate per unit time can be varied over a wide range and adjusted according to the physical properties of the starting compounds and of the reaction products, the temperature and pressure conditions of the first stage being established proceeding from standard pressure and room temperature. It has been found to be particularly appropriate to increase the temperature in two stages and to reduce the pressure in two stages.

The lower limit of the pressure to be established depends on the physical properties, such as boiling points and vapour pressures, of the starting compounds and of the reaction products formed, and is also determined by the plant equipment. Proceeding from standard pressure, it is possible to work stage by stage within these limits with pressures decreasing from stage to stage. The upper temperature limit, typically 280° C., should be complied with in order to avoid the formation of decomposition products, some of which have a damaging effect on colour. The lower limit of the temperature stages is determined by the reaction rate, which must still be sufficiently high to conclude the esterification reaction within an acceptable time. Within these limits, it is possible to work stage by stage with temperatures rising from stage to stage.

The particular reaction conditions, such as temperature, reaction time, pressure to be applied or catalyst to be used, should be tailored to the particular polyol ester, in order to force the formation of colouring components into the background and as far as possible to avoid degradation reactions of the polyol ester with a sufficient reaction rate. Especially in the case of polyol esters based on ether diols, for example triethylene glycol or tetraethylene glycol, enhanced degradation of the ether skeleton may set in when the reaction conditions, such as temperature, reaction time and type and amount of catalyst, are not adjusted in a controlled manner to the particular polyol ester.

The esterification can be undertaken with stoichiometric amounts of polyol and of aliphatic monocarboxylic acid. Preference is given, however, to allowing the polyol to react with excess monocarboxylic acid, which is generally the lower-boiling component and which can be removed by distillation in a simple manner in the subsequent workup of the crude ester. The aliphatic monocarboxylic acid is used in a 10 to 50% molar excess, preferably in a 20 to 40% molar excess, per mole of hydroxyl group to be esterified in the polyol.

The water of reaction formed is distilled out of the reaction vessel in the course of the esterification reaction together with the excess monocarboxylic acid and passed into a downstream phase separator in which monocarboxylic acid and water separate according to their solubility properties. In some cases, the monocarboxylic acid used also forms an azeotrope with water under the reaction conditions and is capable of removing the water of reaction as an entraining agent. The occurrence of water can be used to monitor the progress of the reaction. The water separated out is removed from the process, while the monocarboxylic acid flows out of the phase separator back into the reaction vessel. The addition of a further organic solvent, such as hexane, 1-hexene, cyclohexane, toluene, xylene or xylene isomer mixtures, which assumes the task of the azeotroping agent, is not ruled out, but it is restricted to a few exceptional cases. The azeotroping agent can be added as early as at the start of the esterification reaction or after the attainment of relatively high temperatures. When the theoretically expected amount of water has been obtained or the hydroxyl number, for example determined to DIN 53240, has fallen below a set value, the reaction is ended by allowing the reaction mixture to cool.

The catalysts used for the esterification of the polyol with the monocarboxylic acid are Lewis acids containing at least one element of groups 4 to 14 of the Periodic Table of the Elements, which may be used in solid or liquid form. The term "Lewis acid" in the context of the invention is understood to mean the generally customary definition of those elements or compounds which have an electron vacancy, as explained, for example, in Römpp's Chemie-Lexikon, 8$^{th}$ edition, Franck'sche Verlagshandlung 1983, Volume 3, H-L. The particularly suitable Lewis acids which can be used as catalysts in the esterification reaction include titanium, zirconium, iron, zinc, boron, aluminium or tin, which are used in the form of the element in finely distributed form or preferably in the form of compounds. Suitable compounds are, for example, tin(II) oxide, tin(IV) oxide, tin carboxylates such as tin(II) 2-ethylhexanoate, tin(II) oxalate, tin(II) acetate or tin (IV) acetate, tin(IV) alkoxides such as tetra(methyl) stannate, tetra(ethyl) stannate, tetra(propyl) stannate, tetra(isopropyl) stannate or tetra(isobutyl) stannate, or organotin compounds such as butyltin maleate or dibutyltin dilaurate.

The suitable titanium compounds include alkoxides such as tetra(methyl) orthotitanate, tetra(ethyl) orthotitanate, tetra (propyl) orthotitanate, tetra(isopropyl) orthotitanate, tetra (butyl) orthotitanate, tetra(isobutyl) orthotitanate, tetra(pentyl) orthotitanate or tetra(2-ethylhexyl) orthotitanate; acylates such as hydroxytitanium acetate, hydroxytitanium butyrate or hydroxytitanium pentanoate, or chelates such as tetraethylene glycol titanate or tetrapropylene glycol titanate. It is also possible to successfully use the corresponding zirconium compounds, such as tetra(methyl) orthozirconate, tetra(ethyl) orthozirconate, tetra(propyl) orthozirconate, tetra (isopropyl) orthozirconate, tetra(butyl) orthozirconate, tetra (isobutyl) orthozirconate, tetra(pentyl) orthozirconate or tetra (2-ethylhexyl) orthozirconate.

Likewise suitable are boric acid and boric esters, such as trimethyl borate, triethyl borate, tripropyl borate, triisopropyl borate, tributyl borate or triisobutyl borate.

Likewise suitable are aluminium oxide, aluminium hydroxide, aluminium carboxylates such as aluminium acetate or aluminium stearate, or aluminium alkoxides such as aluminium tributoxide, aluminium tri-sec-butoxide, aluminium tri-tert-butoxide or aluminium triisopropoxide.

It is also possible to use zinc oxide, zinc sulphate and zinc carboxylates such as zinc acetate dihydrate or zinc stearate, and iron(II) acetate or iron(III) hydroxide oxide as catalysts.

The catalyst can be added to the reaction mixture as early as at the start, or only subsequently with observation of safety measures at elevated temperature, when, for example, the removal of the water of reaction has set in.

The amount of the esterification catalyst added is $1 \times 10^{-5}$ to 20 mol %, preferably 0.01 to 5 mol %, especially 0.01 to 2 mol %, based on the starting compound added in deficiency, appropriately based on the polyol. In the case of higher amounts of catalyst, cleavage reactions of the polyol esters are to be expected.

Particularly in the case of the preparation of polyesters based on ether diols, for example triethylene glycol or tetraethylene glycol, in the case of use of high catalyst concentrations toward the end of the reaction and in the phase of the conversion of last residues of free hydroxyl groups, there is a risk of enhanced cleavage of the ether chain, such that the reaction temperature or the pressure to be applied should be adjusted in this case. The higher the catalyst concentration selected is, the lower the reaction temperature or the pressure to be applied should generally be selected, and an optimized temperature and pressure profile should be employed. In the case of excessively low catalyst concentrations, the esterification rate becomes so low that an acceptable conversion is not observed within an acceptable reaction time.

The esterification catalyst can be added in liquid or solid form. Solid catalysts, for example tin(II) oxide, zinc oxide or iron(III) hydroxide oxide are filtered off after the esterification reaction has ended, before the crude polyol ester is subjected to the further workup. When the esterification catalysts are added in the form of liquid compounds, for example tetra(isopropyl) orthotitanate or tetra(butyl) orthotitanate, which are still present dissolved in the reaction mixture after the esterification reaction has ended, these compounds are converted in the course of the workup process, in the steam treatment, to insoluble precipitates which can be filtered off readily.

In the process according to the invention, the esterification will be performed in the presence of an adsorbent. In this case, porous, high-surface area solid materials are used, which are typically used in chemical practice both in the laboratory and in industrial plants. Examples of such materials are high-surface area polysilicic acids such as silica gels (silica xerogels), kieselguhr, high-surface area aluminium oxides and aluminium oxide hydrates, mineral materials such as clays or carbonates, or activated carbon. Activated carbon has been found to be particularly useful. In general, the adsorbent is suspended in finely divided form in the reaction solution, which is agitated by intensive stirring or by introducing an inert gas. This achieves intimate contact between the liquid phase and the adsorbent. The amount of the adsorbent can be adjusted substantially freely and hence according to the individual requirements. Based on 100 parts by weight of the liquid reaction mixture, it is useful to use 0.1 to 5 and preferably 0.1 to 1.5 parts by weight of the adsorbent.

Owing to the quality criteria described at the outset for polyol esters, the process steps in the esterification stage with removal of the water of reaction and in the workup of the crude ester are very important process features, since the adjustment of these process steps influences the sensory and optical properties of the end products to a significant degree. More particularly, an optimized process regime affords polyol esters based on ether diols, for example triethylene glycol or tetraethylene glycol, with high purity, and also low colour number and high colour stability. The structure of the starting materials, of the polyhydric alcohols and of the aliphatic monocarboxylic acids is, in contrast, crucial for the mechanical and thermal properties of the polymer materials plasticized with the polyol esters, and influences the hydrolysis and oxidation stability of lubricants.

The reaction mixture obtained after the reaction has ended comprises, as well as the polyester as the desired reaction product, any unconverted starting materials, more particularly aliphatic monocarboxylic acid still in excess, when the preferred configuration of the process according to the invention with a monocarboxylic acid excess is employed. Typically, unconverted starting compounds present in excess are first distilled off, appropriately with application of a reduced pressure.

Subsequently, the crude ester is subjected to a treatment with steam, which can be done, for example, in simple form by introducing steam into the crude product. One advantage of steam treatment is that catalyst still present is destroyed in the course thereof and converted to hydrolysis products which can be filtered off readily. Since the esterification reaction is performed in the presence of an adsorbent, the adsorbent already present facilitates the deposition of the catalyst conversion products. The presence of an adsorbent during the steam treatment likewise has an advantageous effect on the colour and on the colour stability of the polyol ester. However, it is also possible to filter off the adsorbent after the esterification reaction has ended and excess starting compounds have been removed, i.e. before performance of the steam distillation.

The steam treatment is generally performed at standard pressure, although the employment of a slightly reduced pressure, appropriately down to 400 hPa, is not ruled out. The steam treatment is generally effected at temperatures of 100 to 250° C., preferably of 150 to 220° C. and especially of 170 to 200° C., and is also guided by the physical properties of the polyol esters to be prepared in each case.

In the process step of steam treatment, it is found to be appropriate to proceed in a very gentle manner during the heating period until the attainment of the working temperature, in order to heat the crude ester to the required temperature for the steam treatment.

The duration of the steam treatment can be determined by routine tests and it is generally performed over a period of 0.5 to 5 hours. Too long a steam treatment leads to an undesired increase in the colour number of the polyol ester and should therefore be avoided. An increased degradation reaction of the polyol ester to acidic compounds is also observed, the content of which is manifested in a rise in the neutralization number or acid number, for example determined to DIN EN ISO 3682/ASTM D 1613. In the case of too short a treatment time, the removal of residual acid and water is insufficiently effective, and the desired polyol ester still has too high an undesired acid number and too high a water content. Another observation in the case of too short a treatment time is only a minor advantageous effect on the colour number of the polyol ester.

The conditions in the steam treatment, such as temperature, duration and pressure to be applied, also have to be adjusted precisely to the particular polyol ester, in order to achieve an optimal result in relation to the colour number of the polyol ester and in order to minimize residual contents of starting compounds, water and catalyst traces as far as possible, and simultaneously to suppress degradation reactions. Especially in the case of employment of higher amounts of catalyst and in the case of preparation of polyol esters based on ether diols, for example triethylene glycol or tetraethylene glycol, the conditions in the steam treatment have to be tailored exactly to the particular polyol esters, in order to suppress the undesired degradation of the ether chain.

The steam treatment is optionally followed by the addition of a solid alkaline substance, for example basic silicon dioxide, basic aluminium oxide or sodium carbonate, sodium hydrogencarbonate, calcium carbonate, or sodium hydroxide in solid form, and also basic minerals, in order to further reduce the neutralization number of the polyol ester.

The steam treatment is followed, optionally after filtration of the adsorbent, of any solid alkaline substances added and of further solids obtained, by the drying of the polyol ester, for example by passing an inert gas through the product at elevated temperature. It is also possible to simultaneously apply a reduced pressure at elevated temperature and optionally to pass an inert gas through the product. Even without the action of an inert gas, it is possible to work only at elevated temperature or only under reduced pressure. The particular drying conditions, such as temperature, pressure and time, can be determined by simple preliminary tests. In general, temperatures in the range from 80 to 250° C., preferably 100 to 180° C., are employed at pressures of 0.2 to 500 hPa, preferably 1 to 200 hPa and especially 1 to 20 hPa. Then the crude ester is filtered, if this has not already been done, in order to free it from the solids, any solid alkaline substances added, the hydrolysis products of the catalyst and the adsorbent added in the esterification stage. The filtration is effected in conventional filtering apparatus at standard temperature or at temperatures up to 120° C. The filtration can be supported by common filtration aids such as cellulose, silica gel, kieselguhr, wood flour. However, the use thereof is restricted to exceptional cases.

On completion of the filtration, light-coloured polyol esters are obtained, which also satisfy the other specifications, such as water content, residual acid content, residual content of catalyst constituents and residual content of monoester.

The polyhydric alcohols or polyols used as starting materials for the process according to the invention satisfy the general formula (I)

in which R is an aliphatic or cycloaliphatic hydrocarbon radical having 2 to 20 and preferably 2 to 10 carbon atoms, and n is an integer of 2 to 8, preferably 2, 3, 4, 5 or 6.

Suitable polyols are likewise compounds of the general formula (II)

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer of 1 to 10, preferably 1 to 8 and especially 1, 2, 3 or 4, o is an integer of 2 to 15, preferably 2 to 8 and especially 2, 3, 4 or 5.

Suitable polyols which can be converted by the process according to the invention to light-coloured polyol esters are, for example, 1,3-propanediol, 1,3-butanediol, 1,4-butanediol, neopentyl glycol, 2,2-dimethylolbutane, trimethylolethane, trimethylolpropane, ditrimethylolpropane, trimethylolbutane, 2,2,4-trimethylpentane-1,3-diol, 1,2-hexanediol, 1,6-hexanediol, pentaerythritol or dipentaerythritol or 3(4),8 (9)-dihydroxymethyltricyclo[5.2.1.0$^{2,6}$]decane.

Useful further polyols include ethylene glycol and 1,2-propylene glycol, and the oligomers thereof, especially the ether diols di-, tri- and tetraethylene glycol or dipropylene glycol, tripropylene glycol or tetrapropylene glycol. Ethylene and propylene glycols are industrially produced chemicals. The base substance for preparation thereof is ethylene oxide and propylene oxide, from which 1,2-ethylene glycol and 1,2-propylene glycol are obtained by heating with water under pressure. Diethylene glycol is obtained by ethoxylation from ethylene glycol. Triethylene glycol is obtained, like tetraethylene glycol, as a by-product in the hydrolysis of ethylene oxide to prepare ethylene glycol. Both compounds can also be synthesized by reacting ethylene glycol with ethylene oxide. Dipropylene glycol, tripropylene glycol, tetrapropylene glycol and higher propoxylation products are obtainable from the multiple addition of propylene oxide onto 1,2-propylene glycol.

To obtain light-coloured polyol esters by the process according to the invention, linear or branched, aliphatic monocarboxylic acids having 3 to 20 carbon atoms in the molecule are used. Even though preference is given to saturated acids in many cases, depending on the particular field of use of the plasticizers or lubricants, it is also possible to use unsaturated carboxylic acids as a reaction component for ester synthesis. Examples of monocarboxylic acids as components of polyol esters are propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, cyclohexanecarboxylic acid, 2-ethylhexanoic acid, n-nonanoic acid, 2-methyloctanoic acid, isononanoic acid, 3,5,5-trimethylhexanoic acid, 2-propylheptanoic acid, 2-methylundecanoic acid, isoundecanecarboxylic acid, tricyclodecanecarboxylic acid and isotridecanecarboxylic acid. The novel process has been found to be particularly useful for the preparation of polyol esters of monoethylene glycol, or of the oligomeric ethylene glycols and of 1,2-propylene glycol, or of the oligomeric propylene glycols with $C_4$- to $C_{13}$- or $C_5$- to $C_{10}$-monocarboxylic acids, and for preparation of polyol esters based on 1,3-butanediol, neopentyl glycol, 2,2,4-trimethylpentane-1,3-diol, trimethylolpropane, ditrimethylolpropane, pentaerythritol or 3(4),8(9)-dihydroxymethyltricyclo [5.2.1.0$^{2,6}$]decane.

The polyol esters of ethylene glycol and the oligomers thereof are outstandingly suitable as plasticizers for all common high molecular weight thermoplastic substances. They have been found to be particularly useful as an additive to polyvinyl butyral which is used admixed with glycol esters as an intermediate layer for production of multilayer or composite glasses. They can likewise be used as coalescence agents or film-forming assistants in aqueous dispersions of polymers which find various uses as coating materials. The preparation process according to the invention makes it possible to prepare, in a simple manner, polyol esters with outstanding colour properties which also satisfy further quality demands, such as low odour or a low acid number. The process according to the invention is particularly suitable for preparing triethylene glycol di-2-ethylhexanoate (3G8 Ester), tetraethylene glycol di-n-heptanoate (4G7 Ester), triethylene glycol di-2-ethylbutyrate (3G6 Ester), triethylene glycol di-n-heptanoate (3G7 Ester) or tetraethylene glycol di-2-ethylhexanoate (4G8 Ester).

The process according to the invention can be performed continuously or batchwise in the reaction apparatus typical for chemical technology. Useful apparatus has been found to be stirred tanks or reaction tubes, the batchwise reaction regime being preferred.

The process according to the invention is illustrated in detail in the examples which follow, but it is not restricted to the embodiment described.

WORKING EXAMPLES

Example 1 (Comparative)

Preparation of triethylene glycol di-2-ethylhexanoate (3G8 Ester)

The esterification of triethylene glycol with 2-ethylhexanoic acid was performed in a heatable 2 l four-neck flask equipped with stirrer, internal thermometer and a water separator.

The flask was initially charged with triethylene glycol and 2-ethylhexanoic acid in a 20 mol % excess, based on the hydroxyl group to be esterified, and 1.8 mol % of tetra(isopropyl) orthotitanate, based on triethylene glycol. While stirring and with application of a reduced pressure down to 600 hPa, the mixture was heated to 190° C. and water of reaction formed was removed on the water separator. In this example and those which follow, the occurrence of the first water of reaction was selected as the starting point for the determination of the reaction time. After a reaction time of 2 hours at this stage, the pressure was lowered to 400 hPa and the temperature was increased to 220° C. The course of the reaction was monitored by continuously weighing the water of reaction discharged via the water separator, and by sampling and gas chromatography analysis of the samples. At a content (% by weight) of triethylene glycol di-2-ethylhexanoate, determined by gas chromatography, of at least 97%, and at a residual hydroxyl number of not more than 5.0 mg KOH/g (to DIN 53240), the reaction was ended by cooling the mixture. The esterification time was 6 hours.

Example 2

Preparation of triethylene glycol di-2-ethylhexanoate (3G8 Ester), addition of activated carbon during the esterification Example 2 was carried out in the same way as Example 1, with the sole exception that 0.3% by weight of activated carbon, based on the overall reaction mixture, was added at the start of the esterification reaction. On attainment of the indices reported in Example 1, which characterize the degree of esterification, the reaction was ended. The esterification time was 6 hours.

Example 3

Preparation of triethylene glycol di-2-ethylhexanoate (3G8 Ester), addition of activated carbon during the esterification A heatable 2 l four-neck flask provided with stirrer, internal thermometer and water separator was initially charged with triethylene glycol and 2-ethylhexanoic acid in a 30 mol % excess, based on the hydroxyl group to be esterified, and 0.018 mol % of tetra(isopropyl) orthotitanate, based on triethylene glycol, which were admixed with 1% by weight of activated carbon, based on the overall reaction mixture. While stirring and with application of a reduced pressure down to 600 hPa, the mixture was heated to 220° C. and water of reaction formed was removed on the water separator. After a reaction time of 1 hour at this stage, the pressure was lowered to 400 hPa and the temperature was left at 220° C. After a further 3 hours of reaction time, the pressure was reduced further to 300 hPa. The course of the reaction was monitored by continuously weighing the water of reaction discharged via the water separator and by sampling and gas chromatography analysis of the samples. At a content (% by weight) of triethylene glycol di-2-ethylhexanoate, determined by gas chromatography, of at least 97%, and at a residual hydroxyl number of not more than 5.0 mg KOH/g (to DIN 53240), the reaction was ended by cooling the mixture. The esterification time was 8 hours.

Example 4

Preparation of triethylene glycol di-2-ethylhexanoate (3G8 Ester), addition of activated carbon during the esterification; tin catalysis A heatable 2 l four-neck flask provided with stirrer, internal thermometer and water separator was initially charged with triethylene glycol and 2-ethylhexanoic acid in a 30 mol % excess, based on the hydroxyl group to be esterified, and 0.36 mol % of tin(II) 2-ethylhexanoate, based on triethylene glycol, which were admixed with 0.3% by weight of activated carbon, based on the overall reaction mixture. While stirring and with application of a reduced pressure down to 600 hPa, the mixture was heated to 220° C. and water of reaction formed was removed on the water separator. After a reaction time of 2 hours at this stage, the pressure was lowered to 400 hPa and the temperature was left at 220° C. After a further 4 hours of reaction time, the pressure was reduced further to 300 hPa. The course of the reaction was monitored by continuously weighing the water of reaction discharged via the water separator and by sampling and gas chromatography analysis of the samples. At a content (% by weight) of triethylene glycol di-2-ethylhexanoate, determined by gas chromatography, of at least 97%, and at a residual hydroxyl number of not more than 5.0 mg KOH/g (to DIN 53240), the reaction was ended by cooling the mixture. The esterification time was 6 hours.

Example 5

Preparation of triethylene glycol di-2-ethylhexanoate (3G8 Ester), addition of activated carbon during the esterification, zinc catalysis A heatable 2 l four-neck flask provided with stirrer, internal thermometer and water separator was initially charged with triethylene glycol and 2-ethylhexanoic acid in a 30% excess, based on the hydroxyl group to be esterified, and 0.36 mol % of zinc(II) acetate dihydrate, based on triethylene glycol, which were admixed with 1.0% by weight of activated carbon, based on the overall reaction mixture. While stirring and with application of a reduced pressure down to 600 hPa, the mixture was heated to 220° C. and water of reaction formed was removed on the water separator. After a reaction time of 2 hours at this stage, the pressure was lowered to 400 hPa and the temperature was left at 220° C. The course of the reaction was monitored by continuously weighing the water of reaction discharged via the water separator and by sampling and gas chromatography analysis of the samples. The esterification time was 7 hours.

Workup of the reaction mixtures according to Examples 1 to 5 with the distillative 2-ethylhexanoic acid removal, the steam distillation, the drying and subsequent filtration A) Distillative removal of the excess 2-ethylhexanoic acid down to a residual acid content in the crude ester of <1 mg KOH/g (DIN EN ISO 3682/ASTM D 1613)

| Crude ester according to example | Distillation temperature (°) | Distillation pressure (hPa) |
|---|---|---|
| 1 | 180 | 2 |
| 2 | 180 | 2 |
| 3 | 180 | Beginning at 300 hPa with pressure reduction to 2 hPa over 2 hours |
| 4 | 200 | Beginning at 300 hPa with pressure reduction to 2 hPa over 2 hours |
| 5 | 200 | 2 |

B) Steam distillation (duration in each case 1 hour)

| Crude ester according to example | Bottom temperature (°) | Distillation pressure (hPa) |
|---|---|---|
| 1 | 180 | Standard pressure |
| 2 | 180 | Standard pressure |
| 3 | 180 | Standard pressure |
| 4 | 200 | Standard pressure |
| 5 | 180 | Standard pressure/ duration: 1.5 hours |

C) Drying (duration in each case 0.5 hour)

| Crude ester according to example | Bottom temperature (°) | Pressure (hPa) |
|---|---|---|
| 1 | 140 | 2 |
| 2 | 140 | 2 |
| 3 | 140 | 10 |
| 4 | 160 | 10/duration: 1.5 hours |
| 5 | 160 | 10/duration: 1.5 hours |

D) After filtration of the solids separated out and of the activated carbon added at standard pressure and room temperature, the residue obtained is a light-coloured polyol ester with the following indices:

Gas Chromatography Analysis (% by Weight):

|  | Example 1 % | Example 2 % | Example 3 % | Example 4 % | Example 5 % |
|---|---|---|---|---|---|
| Triethylene glycol di-2-ethylhexanoate | 97.4 | 97.6 | 98.2 | 98.2 | 95.5 |
| Triethylene glycol mono-2-ethylhexanoate | 0.9 | 0.8 | 0.4 | 0.8 | 2.0 |
| Diethylene glycol di-2-ethylhexanoate | 0.4 | 0.5 | 0.4 | 0.3 | 0.6 |
| Remainder | 1.3 | 1.1 | 1.0 | 0.7 | 1.9 |

Indices:

|  | Example 1 | Example 2 | Example 3 | Example 4 | Example 5 |
|---|---|---|---|---|---|
| Hazen colour number (DIN ISO 6271) | 28 | 23 | 16 | 27 | 89 |
| Neutralization number (mg KOH/g, DIN EN ISO 3682/ASTM D 1613) | 0.07 | 0.09 | 0.10 | 0.08 | 0.29 |
| Water content (% by weight, DIN 51777 Part 1) | 0.01 | 0.03 | 0.02 | 0.02 | 0.25 |
| Hydroxyl number (mg KOH/g; DIN 53240) | 2.3 | 2.0 | 1.4 | 1.3 | 3.9 |
| Metal content ppm (DIN EN ISO 11885) | <0.08 | <0.08 | 0.27 | 0.27 | 7.9 |

Example 6

Preparation of neopentyl glycol di-2-ethylhexanoate, addition of activated carbon during the esterification A heatable 2 l four-neck flask provided with stirrer, internal thermometer and water separator was initially charged with neopentyl glycol and 2-ethylhexanoic acid in a 30 mol % excess, based on the hydroxyl group to be esterified, and 0.36 mol % of tetra(isopropyl) orthotitanate, based on neopentyl glycol, which were admixed with 1% by weight of activated carbon, based on the overall reaction mixture. While stirring and with application of a reduced pressure down to 600 hPa, the mixture was heated to 200° C. and water of reaction formed was removed on the water separator. After a reaction time of 2 hours at this stage, the pressure was lowered to 450 hPa and the temperature was left at 200° C. The course of the reaction was monitored by continuously weighing the water of reaction discharged via the water separator and by sampling and gas chromatography analysis of the samples. At a content (% by weight) of neopentyl glycol di-2-ethylhexanoate, determined by gas chromatography, of at least 97%, and at a residual hydroxyl number of not more than 5.0 mg KOH/g (to DIN 53240), the reaction was ended by cooling the mixture. The esterification time was 7 hours.

Thereafter, the excess 2-ethylhexanoic acid was first distilled off at a temperature of 150° C. and at a pressure of 5 hPa. This was followed by a steam distillation at a bottom temperature of 200° C. over a period of 1.5 hours, and then drying at a temperature of 160° C. and at a pressure of 10 hPa over a period of 2 hours. After the solids separated out and the adsorbent added had been filtered, the residue obtained was a light-coloured polyester with the following indices:

Gas Chromatography Analysis (% by Weight):

| Neopentyl glycol di-2-ethylhexanoate | 96.3 |
|---|---|
| Neopentyl glycol mono-2-ethylhexanoate | 2.5 |
| Remainder | 1.2 |

Indices:

| Hazen colour number (DIN ISO 6271) | 32 |
|---|---|
| Neutralization number (mg KOH/g, DIN EN ISO 3682/ASTM D 1613 | 1.21 |
| Water content (% by weight, DIN 51777 Part 1) | 0.1 |
| Hydroxyl number (mg KOH/g; DIN 53240) | 4.5 |
| Metal content ppm (DIN EN ISO 11885) | 0.64 |

The inventive measures of adjusting both the esterification stage and the workup stage in a controlled manner with respect to one another makes it possible to obtain polyol esters with outstanding quality, which enables the use thereof in a multitude of applications.

Example 7 (Comparative)

Preparation of triethylene glycol di-2-ethylhexanoate (3G8 Ester), tin catalysis The esterification of triethylene glycol with 2-ethylhexanoic acid was performed in a heatable 2 l four-neck flask equipped with stirrer, internal thermometer and a water separator.

The flask was initially charged with triethylene glycol and 2-ethylhexanoic acid in a 30 mol % excess, based on the hydroxyl group to be esterified, and 1.8 mol % of tin(II) 2-ethylhexanoate, based on triethylene glycol. While stirring and with application of a reduced pressure down to 600 hPa, the mixture was heated to 220° C. and water of reaction formed was removed on the water separator. After a reaction time of 2 hours at this stage, the pressure was lowered to 400 hPa. The course of the reaction was monitored by continuously weighing the water of reaction discharged via the water separator, and by sampling and gas chromatography analysis of the samples. The esterification was stopped after 5 hours.

In this example, the maximum of triethylene glycol di-2-ethylhexanoate was attained as early as after 2 hours, and the crude reaction mixture has the following composition determined by gas chromatography (calculated free of 2-ethylhexanoic acid):

| | |
|---|---|
| Triethylene glycol di-2-ethylhexanoate | 93.5% by weight |
| Triethylene glycol mono-2-ethylhexanoate | 2.3% by weight |
| Diethylene glycol di-2-ethylhexanoate | 0.6% by weight |
| Remainder | 3.6% by weight |

After 5 hours, the reaction was ended. After removing excess 2-ethylhexanoic acid, the crude polyol ester has the following composition determined by gas chromatography:

| | |
|---|---|
| Triethylene glycol di-2-ethylhexanoate | 86.2% by weight |
| Triethylene glycol mono-2-ethylhexanoate | 0.6% by weight |
| Diethylene glycol di-2-ethylhexanoate | 3.3% by weight |
| Remainder | 9.9% by weight |

The remaining indices were not determined.

As the results of Example 7 show, the maximum of triethylene glycol di-2-ethylhexanoate is attained as early as after 2 hours of esterification time. In the residual conversion phase which follows, predominantly the cleavage of the ether chain occurs with an increase in the content of diethylene glycol di-2-ethylhexanoate and of residual components.

Compared to Example 4, this comparative example demonstrates that an optimized temperature and pressure profile has to be employed at high catalyst concentrations in order to obtain polyol esters of sufficient quality.

While the invention has been described in detail, modifications within the spirit and scope of the invention will be readily apparent to those with skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

The invention claimed is:

1. A process for preparing polyol esters by reacting polyols with linear or branched aliphatic monocarboxylic acids having 3 to 20 carbon atoms, characterized in that a mixture of the starting compounds is allowed to react in the presence of a Lewis acid containing at least one element of groups 4 to 14 of the Periodic Table of the Elements as a catalyst with removal of the water formed, the starting compounds being converted in the presence of an adsorbent, and then a steam treatment is performed in the presence of the adsorbent already present to remove residual acid and water, wherein 0.1 to 5 parts by weight of adsorbent are used per 100 parts by weight of reaction mixture and the adsorbent is activated carbon.

2. The process according to claim 1, characterized in that the mixture of the starting compounds is heated in the presence of the catalyst to a temperature up to a maximum of 280° C., and the pressure is lowered from stage to stage with the temperature kept constant.

3. The process according to claim 1, characterized in that the mixture of the starting compounds is heated in the presence of the catalyst at constant pressure from stage to stage up to a maximum temperature of 280° C.

4. The process according to claim 1, characterized in that the mixture of the starting compounds is heated in the presence of the catalyst at a temperature rising from stage to stage to a maximum of 280° C., and the pressure is also lowered from stage to stage.

5. The process according to claim 4, characterized in that a mixture of the starting compounds is allowed to react in the presence of the catalyst in a first stage at a temperature up to 190° C. and at a pressure up to 600 hPa, and the reaction is conducted to completion in a second stage by increasing the temperature up to 250° C. and at a pressure up to 300 hPa.

6. The process according to claim 1, characterized in that the catalyst is used in an amount of $1.0 \times 10^{-5}$ to 20 mol %, based on the starting compound used in deficiency.

7. The process according to claim 6, characterized in that the catalyst is used in an amount of 0.01 to 5 mol % based on the starting compound used in deficiency.

8. The process according to claim 1, characterized in that the catalyst used is titanium, zirconium, iron, zinc, boron, aluminium or tin in the form of elements or in the form of compounds thereof.

9. The process according to claim 8, characterized in that the tin compounds used are tin(II) oxide, tin(II) oxalate, tin(II) carboxylates, tin(IV) alkoxides or organotin compounds.

10. The process according to claim 8, characterized in that the titanium compounds used are alkoxides, acrylates or chelates.

11. The process according to claim 8, characterized in that the boron compounds used are boric acid or boric esters.

12. The process according to claim 8, characterized in that the aluminium compounds used are aluminium oxide, aluminium hydroxide, aluminium carboxylates or aluminium alkoxides.

13. The process according to claim 8, characterized in that the zinc compounds used are zinc oxide, zinc sulphate or zinc carboxylates.

14. The process according to claim 1, characterized in that the steam treatment is performed at a temperature of 100 to 250° C.

15. The process according to claim 14, characterized in that, after the steam treatment, a solid alkaline substance is added.

16. The process according to claim 15, characterized in that the solid alkaline substance added is basic silicon dioxide, basic aluminium oxide, sodium carbonate, sodium hydrogencarbonate, calcium carbonate, sodium hydroxide or basic minerals.

17. The process according to claim 1, characterized in that the polyol ester, after the steam treatment, is dried at temperatures of 80 to 250° C.—and at pressures of 0.2 to 500 hPa.

18. The process according to claim 16, characterized in that the polyol ester is dried in the presence of an inert gas.

19. The process according to claim 1, characterized in that the polyols used are compounds of the general formula (I)

in which R is an aliphatic or cycloaliphatic hydrocarbon radical having 2 to 20 and n is an integer of 2 to 8.

20. The process according to claim 1, characterized in that the polyols used are compounds of the general formula (II)

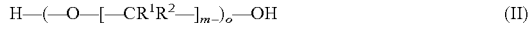

in which $R^1$ and $R^2$ are each independently hydrogen, an alkyl radical having 1 to 5 carbon atoms, or a hydroxyalkyl radical having 1 to 5 carbon atoms, m is an integer of 1 to 10, o is an integer of 2 to 15.

21. The process according to claim 19, characterized in that the polyols used are 1,2-propanediol, 1,3-propanediol, 1,3-butanediol, 1,4-butanediol, neopentyl glycol, 2,2-dimethylolbutane, trimethylolethane, trimethylolpropane, trimethylolbutane, 2,2,4-trimethylpentane-1,3-diol, 1,2-hexanediol, 1,6-hexanediol, pentaerythritol, ethylene glycol or 3(4),8(9)-dihydroxymethyltricyclo[5.2.1.0$^{2,6}$]decane.

22. The process according to claim 20, characterized in that the polyols used are ditrimethylolpropane, dipentaerythritol, diethylene glycol, triethylene glycol, tetraethylene glycol, dipropylene glycol, tripropylene glycol or tetrapropylene glycol.

23. The process according to claim 1, characterized in that the aliphatic monocarboxylic acid converted is propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, 2-ethylhexanoic acid, n-nonanoic acid, 2-methyloctanoic acid, isononanoic acid, 3,5,5-trimethylhexanoic acid or 2-propylheptanoic acid.

24. The process according to claim 1 for preparing triethylene glycol di-2-ethylhexanoate, tetraethylene glycol di-n-heptanoate, triethylene glycol di-2-ethylbutyrate, triethylene glycol di-n-heptanoate or tetraethylene glycol di-2-ethylhexanoate.

25. The process according to claim 1, characterized in that the mixture of the starting compounds is heated in the presence of the catalyst to a temperature up to 250° C., and the pressure is lowered from stage to stage with the temperature kept constant.

26. The process according to claim 6, characterized in that the catalyst is used in an amount of 0.01 to 2 mol %, based on the starting compound used in deficiency.

27. The process according to claim 1 characterized in that 0.1 to 1.5 parts by weight of adsorbent are used per 100 parts by weight of reaction mixture.

28. The process according to claim 14, characterized in that the steam treatment is performed at a temperature of 150 to 220° C.

29. The process according to claim 14, characterized in that the steam treatment is performed at a temperature of 170 to 200° C.

30. The process according to claim 17, characterized in that the polyol ester, after the steam treatment, is dried at temperatures of 100 to 180° C. and at pressures of 1 to 200 hPa.

31. The process according to claim 17, characterized in that the polyol ester, after the steam treatment, is dried at temperatures of 100 to 180° C. and at pressures of 1 to 20 hPa.

32. The process according to claim 19, characterized in that the polyols used are compounds of the general formula (I)

in which R is an aliphatic or cycloaliphatic hydrocarbon radical having 2 to 10 carbon atoms and n is an integer of 2, 3, 4, 5 or 6.

33. The process according to claim 20, characterized in that the polyols used are compounds of the general formula (II)

in which $R^1$ and $R^2$ are each independently hydrogen, methyl, ethyl or propyl, or a hydroxyalkyl radical having 1 to 5 carbon atoms, m is an integer of 1 to 8 and o is an integer of 2 to 8.

34. The process according to claim 20, characterized in that the polyols used are compounds of the general formula (II)

in which $R^1$ and $R^2$ are each independently hydrogen, methyl, ethyl or propyl, or the hydroxymethyl radical, m is an integer of 1, 2, 3 or 4 and o is an integer of 2, 3, 4 or 5.

* * * * *